(12) United States Patent
Lin et al.

(10) Patent No.: US 7,078,520 B2
(45) Date of Patent: Jul. 18, 2006

(54) GLYCOSYLATION OF EXO-GLYCALS

(75) Inventors: Chun-Hung Lin, Taipei (TW); Wen-Bin Yang, Taipei (TW); Hui-Chang Lin, Nan Tou (TW)

(73) Assignee: Academia Sinica, Taipei (TW)

( * ) Notice: Subject to any disclaimer, the term of this patent is extended or adjusted under 35 U.S.C. 154(b) by 432 days.

(21) Appl. No.: 10/406,979

(22) Filed: Apr. 4, 2003

(65) Prior Publication Data

US 2004/0199029 A1 Oct. 7, 2004

(51) Int. Cl.
*C07H 3/02* (2006.01)
*C07C 13/00* (2006.01)

(52) U.S. Cl. .................. 536/124; 536/123.1; 536/1.11; 568/959

(58) Field of Classification Search ............. 536/123.1, 536/124, 1.11; 568/959
See application file for complete search history.

(56) References Cited

OTHER PUBLICATIONS

Lin, H-C, Organic Letters, 2003, 5(&), 1087-1089.*
Chang et al., "Inter- and Intramolecular Alcohol Additions to Exo-glycals", Tetrahedron Letters 43:6515-6519, 2002.
Lin et al., "Steroselective Glycosylation of Exo-Glycals Accelerated by Ferrier-Type Rearrangment", Organic Letters 5:1087-1089, 2003.
Yang et al., "Expeditious Synthesis of C-Glycosyl Conjugated Dienes and Aldehydes from Sugar Lactones", Tetrahedron Letters 42:4657-4660, 2001.
Yang et al., "Facile Synthesis of Conjugated Exo-glycals", Tetrahedron Letters 42:6907-6910, 2001.
Yang et al., "Stereochemistry in the Synthesis and Reaction of Exo-glycals", J. Org. Chem., 67:3773-3782, 2002.

* cited by examiner

*Primary Examiner*—Shaojia A. Jiang
*Assistant Examiner*—Ganapathy Krishnan
(74) *Attorney, Agent, or Firm*—Fish & Richardson P.C.

(57) ABSTRACT

This invention relates to a method of preparing a first alicyclic compound having a vinyl group on one alkyl ring carbon and an alkoxy, cycloalkoxy, heterocycloalkyoxy, aryloxy, or heteroaryloxy group on the same ring carbon; the method comprising reacting an aliphatic alcohol or an aromatic alcohol with a second alicyclic compound having an exo cyclic carbon-carbon double bond, wherein the non-ring olefinic carbon is substituted with a hydroxymethyl, thiomethyl, alkoxymethyl, aryloxymethyl, acyloxymethyl, alkylsulfonyloxymethyl, arylsulfonyloxymethyl, alkylsulfonylmethyl, arylsulfonylmethyl, halomethyl, or silyloxymethyl group.

23 Claims, No Drawings

US 7,078,520 B2

GLYCOSYLATION OF EXO-GLYCALS

BACKGROUND endo-Glycals (1,2-unsaturated sugars) are well recognized as versatile building blocks in preparing numerous biomolecules. In particular, Danishefsky's glycal assembly method offers a novel and efficient approach to synthesize Lewis blood group determinants, gangliosides, and tumor-associated antigens. See e.g., Williams et al., in *Carbohydrates in Chemistry and Biology*, Wiley-VCH Verlag GmbH: Weinheim, Germany, (2000) Volume 1, pp 61–92. 2,3-Unsaturated glycosides have been synthesized from endo-glycals through a Lewis acid-catalyzed allylic rearrangement (Ferrier reaction). They can be readily converted to bioactive products such as forskolin and cyclophellitol. See e.g., Henry et al., J. Org. Chem., (1994) 59:5128 and Fraser-Reid B., Ace. Chem. Res., (1996), 29:57. Recently, Michael addition to 2-nitrogalactal was applied for the synthesis of $T_N$ antigens, $ST_N$ antigens, and other glycopeptides. See e.g., Winterfeld et al., Angew. Chem. Int. Ed. Engl., (2001) 40:2654.

Compared to endo-glycals, there have been few reports on the chemistry of exo-glycals because of their uncommon or tedious preparations.

SUMMARY

This invention is based on the discovery that certain exo-glycals are superior glycosyl donors and undergo glycosylation reactions to give glycosides and glycoconjugates with excellent stereoselectivity.

In one aspect, this invention features a method of preparing a first alicyclic compound having a vinyl group on one alkyl ring carbon and an alkoxy, cycloalkoxy, heterocycloalkyoxy, aryloxy, or heteroaryloxy group on the same ring carbon. The method includes reacting an aliphatic alcohol or an aromatic alcohol with a second alicyclic compound having an exo cyclic carbon-carbon double bond, in which the non-ring olefinic carbon is substituted with a hydroxymethyl, thiomethyl, alkoxymethyl, aryloxymethyl, acyloxymethyl, alkylsulfonyloxymethyl, arylsulfonyloxymethyl, alkylsulfonylmethyl, arylsulfonylmethyl, halomethyl, or silyloxymethyl group.

The term "alkoxy" refers to a linear or branched, saturated or unsaturated non-aromatic $C_1$–$C_{10}$ moiety containing an oxygen radical, such as —$OCH_3$ or —$OCH=C_2H_5$. The term "cycloalkoxy" refers to a saturated or unsaturated $C_3$–$C_{20}$ cyclic moiety containing an oxygen radical, such as —$OC_6H_{11}$ (cyclic). The term "heterocycloalkoxy" refers to a saturated or unsaturated $C_3$–$C_{20}$ cyclic moiety having an oxygen radical and at least one ring heteroatom (e.g., O, N, and S). The term "aryloxy" refers to a moiety having an oxygen radical and at least one aromatic ring, such as phenoxy. The term "heteroaryloxy" refers to a moiety having an oxygen radical and at least one aromatic ring that contains at least one ring heteroatom.

In particular, this invention features a method of preparing a compound having formula (I)

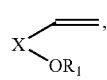

the method includes reacting a compound of formula (II)

with a nucleophile selected from $R_1OH$ in the presence of a Lewis acid, thereby producing a compound having formula (I), in which the bond between X and O is an α-glucosidic bond. In the above formulae, X is a monosaccharide or oligosaccharide residue; $R_1$ is alkyl, cycloalkyl, heterocycloalkyl, aryl, heteroaryl, a monosaccharide or oligosaccharide residue in an aryl-, aralkyl-, alkyl-, ketal-, or acyl-protected form; or an amino acid residue in an aryl-, aralkyl-, alkyl-, or acyl-protected form; and $R_2$ is OH, alkoxy, aryloxy, alkyl sulfonyloxy, aryl sulfonyloxy, alkyl sulfonyl, aryl sulfonyl, silyloxy, SH, F, Cl, Br, I, or OC(O)R'; in which R' is H, alkyl, aralkyl, or aryl. A Lewis acid is any species that is an electron pair acceptor. Examples of Lewis acids include $BF_3 \cdot OEt_2$, $TiCl_4$, $ScCl_3$, $InCl_3$, $BiCl_3$, $Tb(OTf)_3$, $Sc(OTf)_3$, and $LiBF_4$. They can be used in stoichiometric amount or in catalytic amount in the method of the invention.

For example, one care react a compound of formula (II) with a nucleophile to prepare a compound of formula (I). In formula (I) X is a glucose, galactose, fucose, mannose, gulose, or talose residue, in which all hydroxy groups are in a benzyl-protected form and $R_1$ is alkyl, cycloalkyl, a monosaccharide residue in an aryl-, aralkyl-, alkyl-, ketal-, or acyl-protected form; or an amino acid residue in an aryl-, aralkyl-, alkyl-, or acyl-protected form. In formula (II), $R_2$ is OH, alkoxy, alkyl sulfonyl, aryl sulfonyl, silyloxy, SH, Br, I, or OC(O)R'.

The term "alkyl" refers to a linear or branched, saturated or unsaturated non-aromatic $C_1$–$C_{10}$ hydrocarbon moiety, such as —$CH_3$ or —$CH=C_2H_4$. The term "cycloalkyl" refers to a saturated or unsaturated $C_3$–$C_{20}$ cyclic hydrocarbon moiety. The term "heterocycloalkyl" refers to a saturated or unsaturated $C_3$–$C_{20}$ cyclic moiety having at least one ring. The term "aralkyl" refers to an alkyl moiety substituted with aryl or heteroaryl, such as benzyl or pyridinylmethyl. The term "aryl" refers to a hydrocarbon moiety having at least one aromatic ring. Examples of a hydrocarbon aryl moiety include phenyl, phenylene, naphthyl, naphthylene, pyrenyl, anthryl, and phenanthryl. The term "heteroaryl" refers to a moiety having at least one aromatic ring that contains at least one heteroatom. Examples of a heteroaryl moiety include furyl, furylene, fluorenyl, pyrrolyl, thienyl, oxazolyl, imidazolyl, thiazolyl, pyridyl, pyrimidinyl, quinazolinyl, and indolyl. The term "monosaccharide residue" refers to a protected monosaccharide moiety, an oligosaccharide moiety, or an amino acid moiety, in which a few hydrogen and oxygen atoms are missing or replaced with a protecting group. The term "oligosaccharide residue" refers to a protected oligosaccharide moiety, in which a few hydrogen and oxygen atoms are missing or replaced with a protecting group. The term "amino acid residue" refers to a protected amino acid moiety, in which a few hydrogen and oxygen atoms are missing or replaced with a protecting group. Examples of a protecting group include alkyl, aralkyl, aryl, acyl, and ketal.

Alkyl, cycloalkyl, heterocycloalkyl, aryl, heteroaryl, alkoxy, cycloalkoxy, heterocycloalkoxy, aryloxy, heteroaryloxy, and aralkyl mentioned herein include both substituted and unsubstituted moieties. Examples of substituents for cycloalkyl, heterocycloalkyl, aryl, heteroaryl, cycloalkoxy, heterocycloalkoxy, aryloxy, heteroaryloxy, and aralkyl include alkyl, cycloalkyl, heterocycloalkyl, alkoxy, cycloalkoxy, heterocycloalkoxy, aryl, aryloxy, heteroaryl, heteroaryloxy, amino, alkylamino, dialkylamino, arylamino, diarylamino, hydroxyl, halogen, mercapto, alkylmercapto, arylmercapto, cyano, nitro, acyl, acyloxy, and carboxyl. Examples of substituents for alkyl and alkoxy include cycloalkyl, heterocycloalkyl, alkoxy, cycloalkoxy, heterocycloalkoxy, aryl, aryloxy, heteroaryl, heteroaryloxy, amino, alkylamino, dialkylamino, arylamino, diarylamino, hydroxyl, halogen, mercapto, alkylmercapto, arylmercapto, cyano, nitro, acyl, acyloxy, and carboxyl.

In another aspect, this invention features compounds of formula (III)

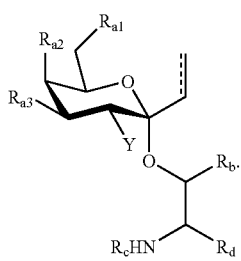

(III)

In the above formula, $=$ is a single bond or a double bond; each of $R_{a1}$, $R_{a2}$, and $R_{a3}$ is, independently, OH or OBn; $R_b$ is H or alkyl; $R_c$ is H, Fmoc, or (O)CR$_e$, in which R$_e$ is alkyl; $R_d$ is COOH, COOMe, or CH(R$_{f1}$)(CR$_{f2}$R$_g$), in which each of R$_{f1}$ and R$_{f2}$ is, independently, OH, acyloxy, or silyloxy, and R$_g$ is alkyl; and Y is OH, OBn, or NHAc. "OBn," "Fmoc," and "NHAc" are abbreviations of benzyl, fluorenylmethyloxycarbonyl, and acetylamino, respectively.

The details of one or more embodiments of the invention are set forth in the accompanying drawings and the description below. Other features, objects, and advantages of the invention will be apparent from the description and from the claims.

DETAILED DESCRIPTION

The method of this invention relates to a glycosylation reaction of exo-glycals. Specifically, in the presence of a Lewis acid (e.g., BF$_3$.OEt$_2$), protected exo-glycals (e.g., benzyl protected gluco- and galacto-type exo-glycals) reacts readily with a variety of alcohols, ranging from simple ones to hindered ones, to give α-glycosidation products.

Two examples are shown below. Compound 1, a gluco-type exo-glycal, reacts with various alcohols to yield compounds 3–7. Similarly, compounds 8–13 can be obtained using compound 2, a galacto-type exo-glycal, as a starting material. The glycosylation of exo-glycals proceeds via an allylic rearrangement. All of the reactions lead to the same stereochemical configuration at the anomeric center, consistent with a nucleophilic attack from the bottom face of the sugar ring.

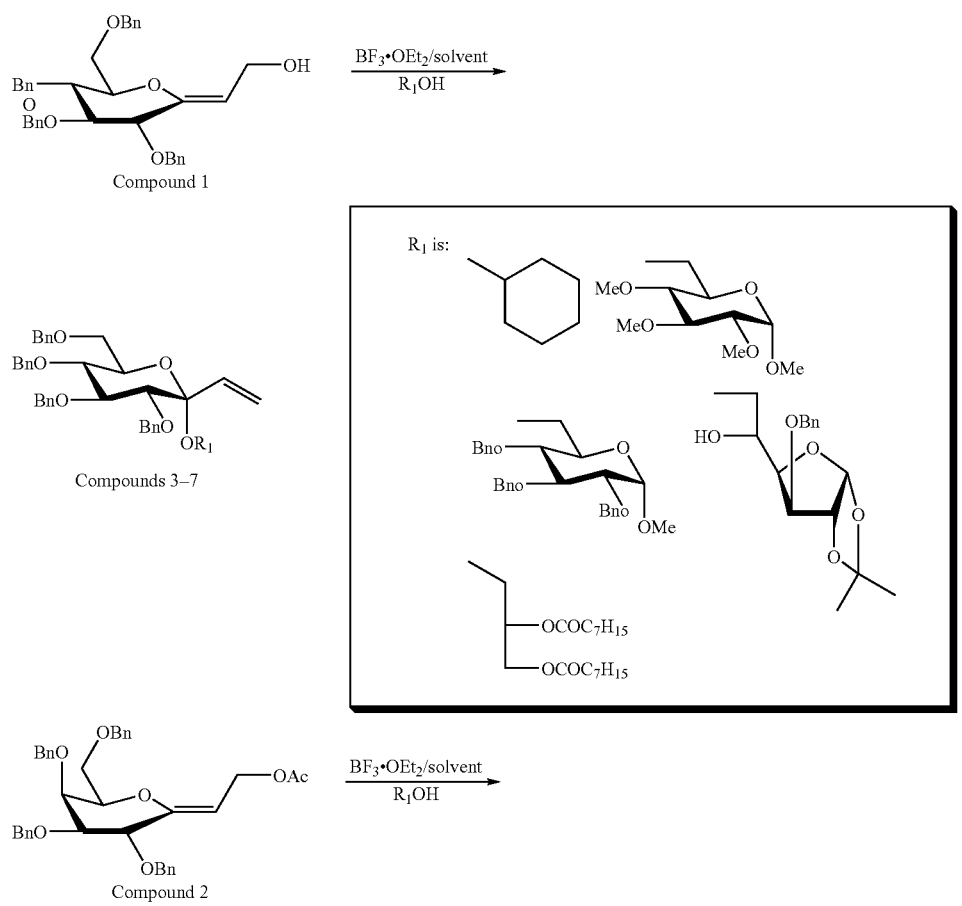

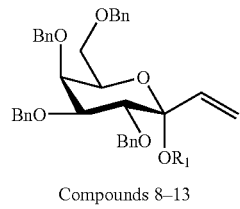
Compounds 8–13
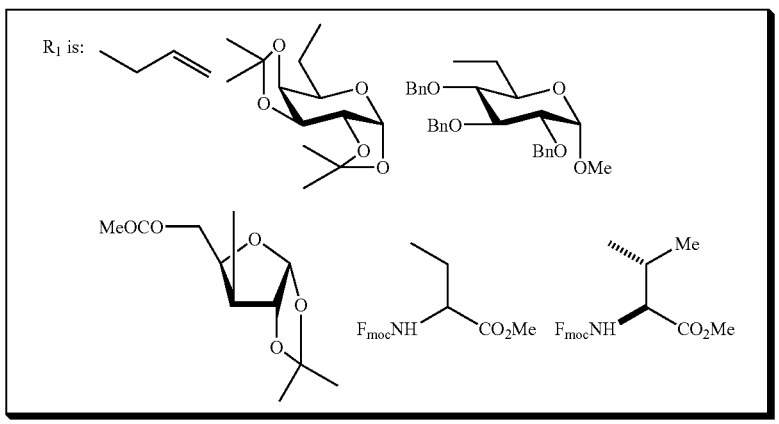
R₁ is:
Shown below are compounds 3–13 prepared using the method of this invention. Details of synthesis of compounds 3–13 are described in Examples 1–11, respectively.
Compound 3
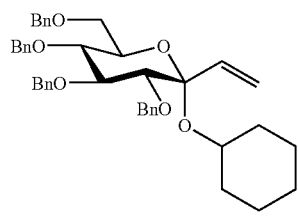
Compound 4
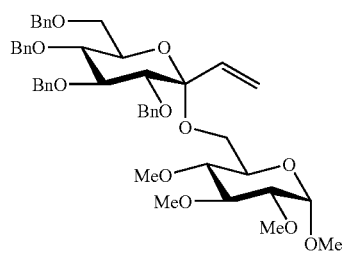
Compound 5
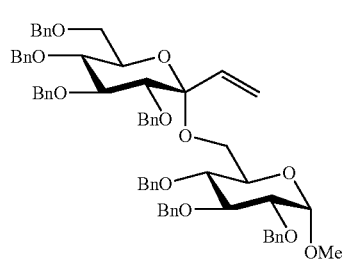
Compound 6
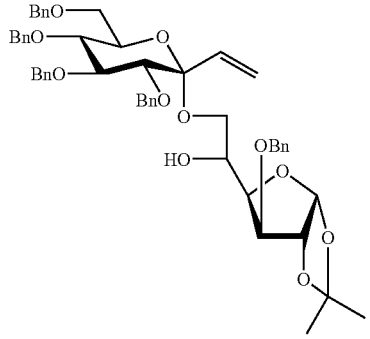
Compound 7
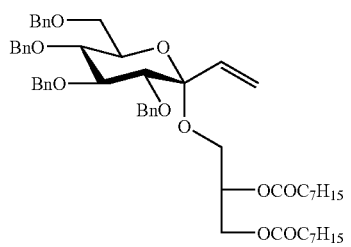
Compound 8
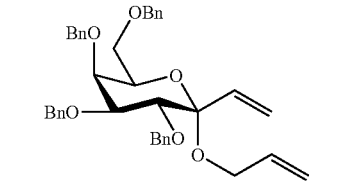
Compound 9
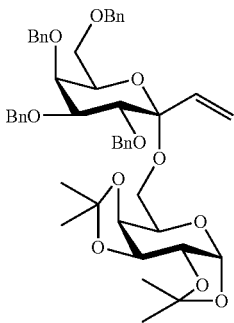

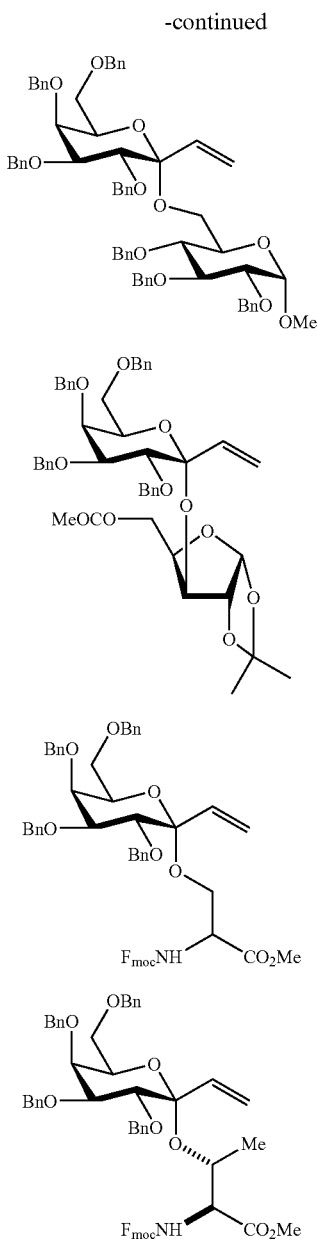

Compound 10

Compound 11

Compound 12

Compound 13

The method of the invention can be used to synthesize simple glycosides (e.g., compound 8), disaccharides (e.g., compounds 4–6 and 9–11), glycolipids (e.g., compound 7) and glycopeptides (e.g., compounds 12 and 13) with high yields. By incorporating both glycosyl donor and acceptor units in the same molecules, disaccharides can serve as glycosyltransferase inhibitors. See Waldscheck et al., Angew. Chem. Int. Ed. Engl., (2001) 40:4007. Glycopeptides mimic the essential core structure of $T_N$ antigen. See e.g., Takahashi et al., Cancer Res., (1998) 48:4361. The vinyl group on each of compounds 3–13 is ready for further transformation(s). For example, compound 9 can be subjected to ozonolysis and followed by the treatment of $Me_2S$ to generate an aldehyde. This aldehyde is a good candidate for conjugation with biomolecules and attachment to solid supports. In another example, compound 8 can be subjected to ozonolysis and a subsequent reductive amination to afford a novel spiro compound. The method of the invention can be used indirectly to achieve α-glycosylation of uronic acids (e.g., sialic acid and 3-deoxyoctulosonic acid). For example, a product of this method can first be converted to an ester, via an aldehyde intermediate, by oxidizing the vinyl group. Such an ester can then be readily converted to a uronic acid.

Also within the scope of the invention are compounds of formula (III) described in the summary section above. These compounds can be prepared by the synthetic method disclosed herein, as well as other suitable methods known in the art. For example, compound 12, a glycopeptide covered by formula (III), can be synthesized by reacting compound 2 with 2-(9H-fluoren-9-yl-methoxycarbonylamino)-3-hydroxy-propionic acid methyl ester in the presence of $BF_3 \cdot OEt_2$. Other protected amino acid derivatives containing a hydroxy group can also be used in this reaction. Compounds of formula (III) possess immuno-modulating properties or can be used as tumor antigens. See e.g., Takahashi et al., Cancer Res. (1988) 48:4361; Hirohashi et al., Proc. Acad. Sci. USA (1985) 82:7039; Federici et al., Int. J. Cancer (1999) 81:193; Ghazizadeh et al., Human Pathol. (1997) 28:960; and Nakada et al., Glycoconjugate J. (1994) 11:262.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE 1

Preparation of Compound 3

A flask containing molecular sieves (4 Å, 3 g) was heated (300° C.) in vacuum for 1 h, cooled down to room temperature, and filled with Argon (g). To this flask were added 2-(3,4,5-tris-benzyloxy-6-benzyloxymethyl-tetrahydro-pyran-2-ylidene)-ethanol (1.0 eq.) (This compound was synthesized by reducing compound 3a described in Yang et al., Tetrahedron Lett. (2001) 42:6907–6910.), cyclohexanol (3.0 eq.), and anhydrous $CH_2Cl_2$ (5 mL). $BF_3 \cdot OEt_2$ (1.0~3.0 eq.) was added dropwise to the above solution at 0° C. while the solution was kept stirred. The reaction was completed within an hour. The reaction mixture was quenched by addition of a saturated $NaHCO_3$ aqueous solution and extracted with $CH_2Cl_2$ for three times (30 mL×3). The collected organic layers were washed with brine, dried over anhydrous $MgSO_4$, and concentrated in vacuo. The resulting residue was subjected to silica gel chromatography with ethyl acetate/hexane to afford compound 3.

$^1$HNMR (400 MHz, $CDCl_3$, δ, ppm): δ 1.10–1.28 (3H, m, cyclohexyl-H), 1.32–1.53 (3H, m, cyclohexyl-H), 1.66–1.77 (2H, m, cyclohexyl-H), 1.79–1.92 (2H, m, cyclohexyl-H), 3.29 (1H, d, J=9.5 Hz, H-2), 3.59–3.68 (1H, m, cyclohexyl-H), 3.64 (1H, t, J=9.6 Hz, H-4), 3.72 (1H, dd, J=11.2, 1.7 Hz, H-6a), 3.82 (1H, dd, J=11.2, 4.2 Hz, H-6b), 4.00 (1H, ddd, J=9.6, 4.2, 1.7 Hz, H-5), 4.11 (1H, t, J=9.5 Hz, H-3), 4.58 (1H, d, J=12.2 Hz, $CH_2Ph$), 4.62 (1H, d, J=11.0 Hz, $CH_2Ph$), 4.65 (1H, d, J=11.5 Hz, $CH_2Ph$), 4.66 (1H, d, J=12.2 Hz, $CH_2Ph$), 4.86 (1H, d, J=10.9 Hz, $CH_2Ph$), 4.89 (1H, d, J=11.0 Hz, $CH_2Ph$), 4.89 (1H, d, J=11.5 Hz, $CH_2Ph$), 4.91 (1H, d, J=10.9 Hz, $CH_2Ph$), 5.21 (1H, dd, J=10.9, 1.9 Hz, H-2'a), 5.58 (1H, dd, J=17.4, 1.9 Hz, H-2'b), 6.05 (1H, dd, J=17.4, 10.9 Hz, H-1'), 7.20–7.38 (20H, m, Ph-H).

$^{13}$CNMR ($CDCl_3$, 100 MHz): δ 24.66, 24.83, 25.59, 34.07, 34.22, 69.18, 71.90, 71.92, 73.45, 75.05, 75.42, 76.73, 78.85, 82.96, 85.35, 99.94, 117.31, 127.48(2×), 127.54, 127.71, 127.73, 127.75, 128.05, 128.26(2×), 128.36 (2×), 128.42, 136.82, 138.40, 138.64, 138.68, 138.92.

EXAMPLE 2

Preparation of Compound 4

Compound 4 was prepared in a manner similar to that described in Example 1.

$^1$HNMR (400 MHz, CDCl$_3$, δ, ppm): δ 2.93 (1H, t, J=9.5 Hz, H-3), 3.12 (1H, dd, J=9.5, 3.6 Hz, H-2), 3.32 (1H, d, J=9.6 Hz, H-2'), 3.35 (3H, s, CH$_3$O), 3.39 (1H, dd, J=10.5, 7.3 Hz, H-6'a), 3.44–3.49 (1H, m, H-4'), 3.47 (6H, s, CH$_3$O× 2), 3.59 (3H, s, CH$_3$O), 3.62–3.77 (5H, m, H-4, H-6a, H-6b, H-5', H-6'b), 3.98 (1H, m, H-5), 4.07 (1H, t, J=9.3 Hz, H-3'), 4.51–4.64 (4H, m, CH$_2$Ph), 4.72 (1H, d, J=3.6 Hz, H-1), 4.77 (1H, d, J=11.0 Hz, CH$_2$Ph), 4.81–4.86 (3H, m, CH$_2$Ph), 5.28 (1H, dd, J=11.2, 1.2 Hz, H-2"a), 5.56 (1H, dd, J=17.5, 1.2 Hz, H-2"b), 5.94 (1H, dd, J=17.5, 11.2 Hz, H-1"), 7.10–7.31 (20H, m, Ph-H).

$^{13}$CNMR (CDCl$_3$, 125 MHz): δ 54.98, 58.90, 60.40, 60.81, 61.48, 69.02, 69.79, 71.54, 73.26, 74.54, 75.31, 75.39, 78.42, 80.44, 81.92, 82.68, 83.75, 84.53, 96.90, 99.47, 118.86, 127.42, 127.47, 127.52, 127.78, 127.83, 128.17, 128.23, 128.30, 135.48, 138.44, 138.59, 138.68, 138.73.

EXAMPLE 3

Preparation of Compound 5

Compound 5 was prepared in a manner similar to that described in Example 1.

$^1$HNMR (CDCl$_3$): δ 3.31–3.37 (3H, m, H-2', 4, 6), 3.35 (3H, s, CH$_3$O), 3.50 (1H, dd, J=9.76, 3.66 Hz, H-2), 3.60 (1H, dd, J=11.29, 1.53 Hz, H-6'), 3.63–3.71 (3H, m, H-6", H-6), 3.81–3.86 (1H, m, H-5), 3.87–3.91 (1H, m, H-5'), 3.98 (1H, t, J=9.15 Hz, H-3), 4.09 (1H, t, J=9.15 Hz, H-3'), 4.48–4.68 (7H, m, CH$_2$Ph, H-1), 4.75–4.89 (7H, m, CH$_2$Ph), 4.96 (1H, d, J=10.99 Hz, CH$_2$Ph), 5.27 (1H, dd, J=10.69, 1.83 Hz, CH$_2$=), 5.54 (1H, dd, J=17.70, 1.83 Hz, CH$_2$=), 5.90 (1H, dd, J=17.70, 10.98 Hz, —CH$_2$=), 7.15–7.36 (35H, m, ArH).

$^{13}$CNMR (CDCl$_3$): δ 54.94 (CH$_3$O), 61.45 (C-6), 68.88 (C-6'), 69.93 (C-5'), 73.20 (two C, CH$_2$Ph), 74.54 (CH$_2$Ph), 74.84 (CH$_2$Ph), 75.18 (CH$_2$Ph), 75.33 (CH$_2$Ph), 75.79 (CH$_2$Ph), 78.39 (C-4'), 78.55 (C-4), 80.16 (C-2), 82.35 (C-3), 82.73 (C-3'), 84.49 (C-2'), 97.51 (C-1), 99.58 (C-1'), 118.94 (CH$_2$=), 127.37 (Ph), 127.38 (Ph), 127.45 (Ph), 127.49 (Ph), 127.57 (Ph), 127.60 (Ph), 127.79 (Ph), 127.84 (Ph), 127.95 (Ph), 128.01 (Ph), 128.12 (Ph), 128.19 (Ph), 128.27 (Ph), 128.34 (Ph), 128.37 (Ph), 128.40 (Ph), 135.42 (—CH=), 138.22 (Ph), 138.27 (Ph), 138.48 (Ph), 138.54 (Ph), 138.67 (Ph), 138.71 (Ph).

EXAMPLE 4

Preparation of Compound 6

Compound 6 was prepared in a manner similar to that described in Example 1.

$^1$HNMR (400 MHz, CDCl$_3$, δ, ppm): δ 1.25 (3H, s, H—CH$_3$), 1.35 (3H, s, H—CH$_3$), 3.38 (1H, d, J=9.6 Hz, H-2'), 3.52 (1H, dd, J=10.2, 4.6 Hz, H-6), 3.67 (1H, dd, J=10.2, 2.8 Hz, H-6), 3.70 (1H, dd, J=11.2, 2.0 Hz, H-6'), 3.71 (1H, t, J=9.7 Hz, H-4'), 3.83 (1H, J=11.2, 3.6 Hz, H-6'), 3.91 (1H, ddd, J=10.0, 3.6, 2.0 Hz, H-5'), 4.04 (1H, t, J=9.3 Hz, H-3'), 4.09 (1H, d, J=2.8 Hz, H-2), 4.10–4.16 (1H, m, H-5), 4.18 (1H, dd, J=2.8, 8.8 Hz, H-3), 4.53–4.60 (2H, m, —CH$_2$-Ph), 4.56 (1H, t, J=9.0 Hz, H-4), 4.61–4.69 (4H, m, —CH$_2$-Ph), 4.81–4.85 (4H, m, —CH$_2$-Ph), 5.32 (1H, dd, J=1.7, 10.9 Hz, H-2a"), 5.58 (1H, dd, J=1.7, 17.4 Hz, H-2b"), 5.87 (1H, d, J=3.5 Hz, H-1), 5.90 (1H, dd, J=17.4, 10.9 Hz, H-1"), 7.20–7.35 (25H, m, ArH).

$^{13}$CNMR (100 MHz, CDCl$_3$): δ 26.31, 26.94, 63.25, 67.47, 68.73, 71.48, 72.45, 73.28, 74.75, 75.54, 75.93, 78.42, 79.72, 81.76, 82.46, 83.19, 84.64, 99.29, 105.16, 111.74, 127.46, 127.51, 127.62, 127.71, 127.74, 127.78, 127.80, 127.87, 128.03, 128.19, 128.31, 128.34, 128.47, 128.75, 135.05, 137.61, 138.01, 138.53, 138.56, 138.75.

EXAMPLE 5

Preparation of Compound 7

Compound 7 was prepared in a manner similar to that described in Example 1.

$^1$HNMR (400 MHz, CDCl$_3$, δ, ppm): δ 0.85–0.88 (6H, m, H—CH$_3$), 1.20–1.30 (16H, m, H—CH$_2$), 3.33 (1H, d, J=9.5 Hz, H-2'), 3.44 (1H, dd, J-10.6, 5.3 Hz, H-6a'), 3.56 (1H, dd, J=10.6, 5.3 Hz, H-6b'), 3.61–3.77 (4H, m, H-4', 5', —CH$_2$—O—), 4.05 (1H, t, J=9.3Hz, H-3'), 4.20 (1H, dd, J=11.9, 6.2 Hz, H—CH$_2$—O—), 4.39 (1H, dd, J=11.9, 3.7 Hz, H—CH$_2$—O—), 4.53–4.64 (4H, m, H—CH$_2$Ph), 4.80–4.89 (4H, m, H—CH$_2$Ph), 5.18–5.24 (1H, m, H—CH—O—), 5.32 (1H, dd, J=10.9, 1.8 Hz, H-2a"), 5.57 (1H, dd, J=17.4, 1.8 Hz, H-2b"), 5.89 (1H, dd, J=17.4, 10.9 Hx, H-1"), 7.20–7.36 (20H, m, ArH).

$^{13}$CNMR (100 MHz, CDCl$_3$): δ 14.03, 22.58, 24.85, 28.91, 29.05, 29.68, 31.65, 34.11, 34.27, 62.64, 68.81, 69.91, 72.06, 73.40, 74.86, 75.41, 75.53, 78.29, 82.81, 84.29, 99.57, 119.28, 127.53, 127.59, 127.61, 127.79, 128.24, 128.33×2, 134.79, 138.38×3, 138.71, 172.99, 173.39.

EXAMPLE 6

Preparation of Compound 8

Compound 8 was prepared in a manner similar to that described in Example 1.

$^1$HNMR (400 MHz, CDCl$_3$, δ, ppm): δ 7.35–7.25 (20H, m, ArH), 5.97–5.87 (2H, m, H-1',2"), 5.51 (1H, dd, J=17.6, 1.6 Hz, H-2'a), 5.24 (1H, dd, J=11.2, 1.6 Hz, H-2'), 5.55 (1H, dd, J=17.2, 1.6 Hz, H-3"a), 5.08 (1H, d, J=10.4 Hz, H-3"b), 4.94 (1H, d, J=11.6 Hz, CH$_2$Ph), 4.86 (1H, d, J=11.2 Hz, CH$_2$Ph), 4.75 (1H, d, J=11.6 Hz, CH$_2$Ph), 4.71 (1H, d, J=11.6 Hz, CH$_2$Ph), 4.63 (1H, d, J=11.2 Hz, CH$_2$Ph), 4.60 (1H, d, J=11.6 Hz, CH$_2$Ph), 4.49 (1H, d, J=12 Hz, CH$_2$Ph), 4.44 (1H, d, J=12 Hz, CH$_2$Ph), 4.09 (1H, dd, J=10, 2.8 Hz, H-3), 3.99 (1H, d, J=2.8 Hz, H-4), 3.97–3.84 (3H, m, H-5, 6a,b), 3.62 (1H, dd, J=9.6, 7.2 Hz, H-1"a), 3.58 (1H, dd, J=9.6, 6 Hz, H-1"b).

$^{13}$CNMR (CDCl$_3$, 100 MHz): δ 138.97, 138.74, 138.44, 138.15, 135.26, 135.09, 128.35, 128.31, 128.15, 128.10, 127.97, 127.65, 127.63, 127.44, 127.41, 118.61, 116.25, 100.22, 80.40, 80.33, 75.73, 75.05, 74.49, 73.39, 72.89, 70.43, 69.01, 63.02.

EXAMPLE 7

Preparation of Compound 9

Compound 9 was prepared in a manner similar to that described in Example 1.

$^1$HNMR (400 MHz, CDCl$_3$, δ, ppm): δ 7.35–7.23 (20H, m, ArH), 5.95 (1H, dd, J=17.6, 11.2 Hz, H-1"), 5.52 (1H, dd, J=17.6, 2.0 Hz, H-2"a), 5.48 (1H, d, J=4.8 Hz, H-1), 5.23 (1H, dd, J=11.2, 2.0 Hz, H-2"b), 4.92 (1H, d, J=11.6 Hz, CH$_2$Ph), 4.87 (1H, d, J=11.2 Hz, CH$_2$Ph), 4.71 (2H, s, CH$_2$Ph), 4.61 (1H, d, J=11.6 Hz, CH$_2$Ph), 4.60 (1H, d, J=11.6 Hz, CH$_2$Ph), 4.55 (1H, dd, J=8.0, 2.4 Hz, H-3), 4.51 (1H, d, J=11.6 Hz, CH$_2$Ph), 4.45 (1H, d, J=12 Hz, CH$_2$Ph), 4.27–4.23 (2H, m, H-2,4), 4.17–4.14 (1H, m, H-5'), 4.10 (1H, dd, J=10, 3.2 Hz, H-3'), 4.02 (1H, dd, J=3.2, 1.2 Hz, H-4'), 4.00–3.97 (1H, m, H-5), 3.84 (1H, d, J=10 Hz, H-2'), 3.68 (1H, dd, J=9.2, 8 Hz, H-6'a), 3.61 (1H, dd, J=10.8, 5.2 Hz, H-6a), 3.56 (1H, dd, J=9.2, 5.6 Hz, H-6'b), 3.50 (1H, dd, J=10.8, 6.8 Hz, H-6b).

$^{13}$CNMR (CDCl$_3$, 100 MHz): δ 139.18, 138.84, 138.73, 138.36, 135.38, 128.30, 128.26, 128.10, 128.06, 127.89, 127.72, 127.52, 127.47, 127.33, 127.31, 118.70, 109.11, 108.44, 99.96, 96.27, 80.57, 80.21, 75.35, 75.03, 74.49, 73.19, 72.66, 71.32, 70.75, 70.71, 69.73, 68.68, 67.39, 61.35, 26.11, 25.96, 24.98, 24.46.

EXAMPLE 8

Preparation of Compound 10

Compound 10 was prepared in a manner similar to that described in Example 1.

$^1$HNMR (400 MHz, CDCl$_3$, δ, ppm): δ 7.33–7.18 (40H, m, ArH), 5.87 (1H, dd, J=17.6, 10.8 Hz, H-1"), 5.48 (1H, dd, J=17.6, 1.6 Hz, H-2"a), 5.22 (1H, dd, J=10.8, 2 Hz, H-2"b), 4.94 (1H, d, J=10.8 Hz, CH$_2$Ph), 4.93 (1H, d, J=11.6 Hz, CH$_2$Ph), 4.87 (1H, d, J=11.2 Hz, CH$_2$Ph), 4.79 (1H, d, J=10.8 Hz, CH$_2$Ph), 4.77 (1H, d, J=10.8 Hz, CH$_2$Ph), 4.73 (1H, d, J=12 Hz, CH$_2$Ph), 4.67 (2H, brs, CH$_2$Ph), 4.62 (1H, d, J=12.4 Hz, CH$_2$Ph), 4.59 (1H, d, J=11.6 Hz, CH$_2$Ph), 4.59 (1H, d, J=12.8 Hz, CH$_2$Ph), 4.54 (1H, d, J=3.2 Hz, H-1), 4.46 (1H, d, J=11.2 Hz, CH$_2$Ph), 4.44 (1H, d, J=12 Hz, CH$_2$Ph), 4.39 (1H, d, J=12 Hz, CH$_2$Ph), 4.03–3.98 (2H, m, H-3',5'), 3.9–3.91 (2H, m, H-3,4'), 3.82 (1H, d, J=10 Hz, H-2'), 3.83–3.79 (1H, m, H-5), 3.69 (1H, dd, J=10.8, 1.6 Hz, H-6a), 3.58 (1H, dd, J=9.2, 6.8 Hz, H-6'a), 3.53 (1H, dd, J=9.6, 6 Hz, H-6'b), 3.46 (1H, dd, J=9.6, 3.6 Hz, H-2), 3.32–3.22 (2H, m, H-6b, 4), 3.22 (3H, S, CH$_3$O).

$^{13}$CNMR (CDCl$_3$, 100 MHz): δ 139.03, 138.78, 138.69, 138.34, 138.22, 135.21, 128.41, 128.34, 128.31, 128.29, 128.15, 128.06, 127.95, 127.86, 127.80, 127.70, 127.59, 127.55, 127.50, 127.41, 127.39, 127.29, 118.89, 99.95, 97.45, 82.26, 80.56, 80.10, 79.69, 78.89, 75.74, 75.23, 75.14, 74.89, 74.45, 73.18, 73.12, 72.48, 70.13, 69.96, 69.01, 61.64, 54.72.

EXAMPLE 9

Preparation of Compound 11

Compound 11 was prepared in a manner similar to that described in Example 1.

$^1$HNMR (400 MHz, CDCl$_3$, δ, ppm): δ 7.34–7.23 (20H, m, ArH), 5.98 (1H, dd, J=17.2, 10.8 Hz), 5.86 (1H, d, J=3.6 Hz), 5.71 (1H, dd, J=17.2, 1.6 Hz), 5.41 (1H, dd, J=10.8, 1.6 Hz), 4.93 (1H, d, J=12 Hz, CH$_2$Ph), 4.91 (1H, d, J=11.6 Hz, CH$_2$Ph), 4.86 (1H, d, J=3.6 Hz), 4.72 (1H, d, J=11.6 Hz, CH$_2$Ph), 4.68 (1H, d, J=11.6 Hz, CH$_2$Ph), 4.60 (1H, d, J=11.6 Hz, CH$_2$Ph), 4.59 (1H, d, J=11.6 Hz, CH$_2$Ph), 4.46 (2H, brs), 4.44–4.37 (3H, m), 4.34 (1H, d, J=2.8 Hz), 3.95 (1H, dd, J=10.4, 2.8 Hz), 3.94–3.92 (1H, m), 3.87 (1H, d, J=1.6 Hz), 3.79 (1H, d, J=10 Hz), 3.75 (3H, s), 3.61 (1H, dd, J=9.6, 7.2 Hz), 3.41 (1H, d, J=10, 4.4 Hz), 1.42 (3H, s), 1.08 (3H, s).

$^{13}$CNMR (CDCl$_3$, 100 MHz): δ 155.50, 138.72, 138.60, 138.39, 137.96, 133.75, 128.41, 128.35, 128.21, 128.19, 128.15, 127.72, 127.69, 127.61, 127.55, 127.53, 127.15, 120.20, 111.47, 105.13, 100.74, 82.45, 80.89, 79.89, 78.18, 77.06, 75.35, 74.93, 74.27, 73.57, 73.02, 71.32, 70.14, 65.78, 54.72, 26.61, 25.91.

EXAMPLE 10

Preparation of Compound 12

Compound 12 was prepared in a manner similar to that described in Example 1.

$^1$HNMR (400 MHz, CDCl$_3$, δ, ppm): δ 7.74 (2H, d, J=7.6 Hz, ArH), 7.56 (2H, dd, J=6.8, 6.8 Hz, ArH), 7.38–7.21 (24H, m, ArH), 5.88 (1H, d, J=8.4 Hz, NH), 5.83 (1H, dd, J=17.6, 11.2 Hz, H-1"), 5.52 (1H, dd, J=17.6, 1.6 Hz, H-2a"), 5.30 (1H, dd, J=11.2, 1.6 Hz, H-2b"), 4.93 (1H, d, J=11.6 Hz, CH$_2$Ph), 4.88 (1H, d, J=11.2 Hz, CH$_2$Ph), 4.72 (2H, brs, CH$_2$Ph), 4.59 (1H, d, J=12 Hz, CH$_2$Ph), 4.56 (1H, d, J=12 Hz, CH$_2$Ph), 4.55–4.51 (1H, m, H-2'), 4.45 (1H, d, J=11.6 Hz, CH$_2$Ph), 4.40 (1H, d, J=12.0 Hz, CH$_2$Ph), 4.38 (1H, dd, J=10.0, 7.2 Hz, H-6a'), 4.30 (1H, dd, J=10, 6.8 Hz, H-6b'), 4.20 (1H, dd, J=7.2, 6.8 Hz, H-7'), 3.99 (1H, dd, J=10, 2 Hz, H-3), 3.97 (1H, brs, H-4), 3.89–3.83 (2H, m, H-1',5), 3.82 (1H, d, J=9.6 Hz, H-2), 3.64 (4H, brs, H-6a, 4'), 3.58–3.56 (2H, m, H-1', 6b).

$^{13}$CNMR (CDCl$_3$, 100 MHz): δ 170.76, 155.98, 143.90, 143.85, 141.25, 138.81, 138.70, 138.49, 137.99, 134.43, 128.33, 128.18, 128.13, 127.97, 127.68, 127.64, 127.61, 127.55, 127.50, 127.32, 127.02, 125.10, 119.91, 119.38, 99.91, 80.43, 79.74, 75.32, 74.64, 74.42, 73.38, 72.68, 70.76, 69.03, 67.10, 62.31, 54.36, 52.36, 47.10.

EXAMPLE 11

Preparation of Compound 13

Compound 13 was prepared in a manner similar to that described in Example 1.

$^1$HNMR (400 MHz, CDCl$_3$, δ, ppm): δ 7.74 (2H, d, J=7.6 Hz, ArH), 7.60 (2H, dd, J=7.2, 2.8 Hz, ArH), 7.37–7.21 (24H, m, ArH), 5.87 (1H, dd, J -17.2, 10.8 Hz), 5.71 (1H, d, J=9.2 Hz), 5.58 (1H, dd, J=17.6, 1.2 Hz), 5.30 (1H, dd, J=10.8, 1.2 Hz), 4.94 (1H, d, J=11.6 Hz, CH$_2$Ph), 4.87 (1H, d, J=10.8 Hz, CH$_2$Ph), 4.75 (2H, brs), 4.61 (1H, d, J=11.6 Hz, CH$_2$Ph), 5.54 (1H, d, J=11.2 Hz, CH$_2$Ph), 4.50–4.33 (5H, m), 4.26–4.23 (2H, m), 4.05–3.98 (3H, m), 3.75 (1H, d, J=9.6 Hz), 3.64 (1H, dd, J=9.2, 7.2 Hz), 3.54 (1H, dd, J=8.8, 5.6 Hz), 3.45 (3H, s), 1.21 (3H, d, J=6.4 Hz).

$^{13}$CNMR (CDCl$_3$, 100 MHz): δ 170.82, 156.72, 144.00, 143.82, 141.28, 138.97, 138.53, 138.50, 138.03, 134.47, 128.39, 128.35, 128.17, 128.15, 128.11, 127.89, 127.69, 127.66, 127.52, 127.44, 127.40, 127.08, 127.04, 125.17, 125.12, 119.93, 119.03, 100.38, 81.07, 79.68, 75.76, 74.74, 74.47, 73.51, 72.52, 70.39, 69.89, 68.87, 67.13, 59.59, 52.11, 47.20, 18.79.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method of preparing a first alicyclic compound having a vinyl group on one ring carbon and an alkoxy, cycloalkoxy, heterocycloalkyoxy, aryloxy, or heteroaryloxy group on the same ring carbon; the method comprising reacting an aliphatic alcohol or an aromatic alcohol with a second alicyclic compound having an exo cyclic carbon-carbon double bond, wherein the non-ring olefinic carbon is substituted with a hydroxymethyl, thiomethyl, alkoxymethyl, aryloxymethyl, acyloxymethyl, alkylsulfonyloxymethyl, arylsulfonyloxymethyl, alkylsulfonylmethyl, arylsulfonylmethyl, halomethyl, or silyloxymethyl group.

2. The method of claim 1, the method comprising reacting an aliphatic alcohol with the second alicyclic compound, wherein the second alicyclic compound is a glucose-, galactose-, fucose-, mannose-, gulose-, or talose-based exo-glycal, in which all hydroxy groups are in an aryl-, aralkyl-, or alkyl-protected form, the non-ring olefinic carbon of the second alicyclic compound is substituted with a hydroxymethyl or acetoxymethyl group.

3. The method of claim 2, wherein the aliphatic alcohol is optionally substituted with one or more hydroxy, methoxy, benzyloxy, acyloxy, methoxycarbonyl, or Fmoc groups, the second alicyclic compound is a glucose-based exo-glycal, in which all hydroxy groups are in a benzyl-protected form, and the non-ring olefinic carbon of the second alicyclic compound is substituted with a hydroxymethyl group.

4. The method of claim 2, wherein the aliphatic alcohol is optionally substituted with one or more hydroxy, methoxy, benzyloxy, acyloxy, methoxycarbonyl, or Fmoc groups, the second alicyclic compound is a galactose-based exo-glycal, in which all hydroxy groups are in a benzyl-protected form, and the non-ring olefinic carbon of the second alicyclic compound is substituted with an acetoxylmethyl group.

5. A method of preparing a compound having the formula

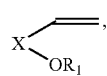
(I)

the method comprising:
reacting a compound of the formula

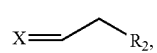
(II)

with a nucleophile selected from $R_1OH$ in the presence of a Lewis acid; wherein
- X is a monosaccharide or oligosaccharide residue;
- $R_1$ is alkyl, cycloalkyl, heterocycloalkyl, aryl, heteroaryl, a monosaccharide or oligosaccharide residue, in an aryl-, aralkyl-, alkyl-, ketal-, or acyl-protected form; or an amino acid residue in an aryl-, aralkyl-, alkyl-, or acyl-protected form; and
- $R_2$ is OH, alkoxy, aryloxy, alkyl sulfonyloxy, aryl sulfonyloxy, alkyl sulfonyl, aryl sulfonyl, silyloxy, SH, F, Cl, Br, I, or OC(O)R'; in which R' is H, alkyl, aralkyl, or aryl; thereby producing a compound having formula (I) in which the bond between X and O is an α-glucosidic bond.

6. The method of claim 5, wherein
- X is a glucose, galactose, fucose, mannose, gulose, or talose residue, in which all hydroxy groups are in a benzyl-protected form;
- $R_1$ is alkyl, cycloalkyl, a monosaccharide residue in an aryl-, aralkyl-, alkyl-, ketal-, or acyl-protected form; or an amino acid residue in an aryl-, aralkyl-, alkyl-, or acyl-protected form; and
- $R_2$ is OH, alkoxy, alkyl sulfonyl, aryl sulfonyl, silyloxy, SH, Br, I, or OC(O)R'.

7. The method of claim 6, wherein
- X is a glucose residue, in which all hydroxy groups are in a benzyl-protected form;
- $R_1$ is cycloalkyl or a monosaccharide residue in an aryl-, aralkyl-, alkyl-, ketal-, or acyl-protected form; and
- $R_2$ is OH.

8. The method of claim 6, wherein
- X is a galactose residue, in which all hydroxy groups are in a benzyl-protected form;
- $R_1$ is alkyl, a monosaccharide residue in an aryl-, aralkyl-, alkyl-, ketal-, or acyl-protected form; or an amino acid residue in an aryl-, aralkyl-, alkyl-, or acyl-protected form; and
- $R_2$ is OAc.

9. The method of claim 7, wherein $R_1$ is cyclohexyl.

10. The method of claim 7, wherein $R_1$ is a glucopyranose residue, in which the hydroxy groups at 1-, 2-, 3-, and 4-positions are in a methyl-protected form.

11. The method of claim 7, wherein $R_1$ is a glucopyranose residue, in which the hydroxy group at 1-position is in a methyl-protected form and the hydroxy groups at 2-, 3-, and 4-positions are in a benzyl-protected form.

12. The method of claim 7, wherein $R_1$ is a glucofuranose reside, in which the hydroxy groups at 1- and 2-positions are in an ketal-protected form and the hydroxy group at 3-position is in a benzyl-protected form.

13. The method of claim 7, wherein $R_1$ is propyl substituted with two $OC(O)C_7H_{15}$ groups at 2- and 3-positions.

14. The method of claim 8, wherein $R_1$ is allyl.

15. The method of claim 8, wherein $R_1$ is a galactopyranose residue, in which both the hydroxy groups at 1- and 2- and the hydroxy groups at 3- and 4-positions are in an ketal-protected form.

16. The method of claim 8, wherein $R_1$ is a glucopyranose residue, in which the hydroxy group at 1-position is in a methyl-protected form and the hydroxy groups at 2-, 3-, and 4-positions are in a benzyl-protected form.

17. The method of claim 8, wherein $R_1$ is a xylofuranose residue, in which the hydroxy groups at 1- and 2-positions are in an ketal-protected form and the hydroxy group at 4-position is in an acyl-protected form.

18. The method of claim 8, wherein $R_1$ is a seine residue, in which the amino group is in a Fmoc-protected form and the carboxy group is in a methyl-protected form.

19. The method of claim 8, wherein $R_1$ is a threonine residue, in which the amino group is in a Fmoc-protected form and the carboxy group is in a methyl-protected form.

20. A compound having the following formula

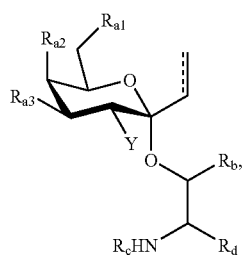

(III)

wherein
- ⚌ is a single bond or a double bond;
- each of $R_{a1}$, $R_{a2}$, and $R_{a3}$ is, independently, OH or OBn;
- $R_b$ is H or alkyl;
- $R_c$ is H, Fmoc, or (O)CR$_e$, in which $R_e$ is alkyl;
- $R_d$ is COOH, COOMe, or CH($R_{f1}$)(CR$_{f2}$R$_g$), in which each of $R_{f1}$ and $R_{f2}$ is, independently, OH, acyloxy or silyloxy, and $R_g$ is alkyl; and
- Y is OH, OBn, or NHAc.

21. The compound of claim 20, wherein
- ⚌ is a single bond or a double bond;
- each of $R_{a1}$, $R_{a2}$, and $R_{a3}$ is OBn;
- $R_b$ is H or alkyl;
- $R_c$ is Fmoc;
- $R_d$ is COOMe; and
- Y is OBn or NHAc.

22. The compound of claim 20, wherein
- ⚌ is a single bond or a double bond;
- each of $R_{a1}$, $R_{a2}$, and $R_{a3}$ is OH;
- $R_b$ is H or alkyl;
- $R_c$ is H;
- $R_d$ is COOH; and
- Y is OH or NHAc.

23. The compound of claim 20, wherein
- ⚌ is a single bond or a double bond;
- each of $R_{a1}$, $R_{a2}$, and $R_{a3}$ is OH or OBn;
- $R_b$ is H;
- $R_c$ is (O)CR$_e$, in which $R_e$ is alkyl;
- $R_d$ is CH($R_{f1}$)(CR$_{f2}$R$_g$), in which each of $R_{f1}$ and $R_{f2}$ is, independently, OH, acyloxy, or silyloxy, and $R_g$ is alkyl; and
- Y is OH or OBn.

* * * * *